United States Patent
Bingham et al.

(10) Patent No.: US 6,482,225 B1
(45) Date of Patent: Nov. 19, 2002

(54) OSMOPHORE-PACIFIER

(76) Inventors: Peter M. Bingham, 59 Lower English Settlement Rd., Underhill, VT (US) 05489; Emidio Marco Sivieri, 8312 Shawnee St., Philadelphia, PA (US) 19118

( * ) Notice: Subject to any disclaimer, the term of this patent is extended or adjusted under 35 U.S.C. 154(b) by 0 days.

(21) Appl. No.: 10/039,882

(22) Filed: Jan. 3, 2002

Related U.S. Application Data

(63) Continuation of application No. 09/516,372, filed on Mar. 1, 2000, now abandoned.
(60) Provisional application No. 60/122,333, filed on Mar. 2, 1999.

(51) Int. Cl.$^7$ ................................................. A61J 17/00
(52) U.S. Cl. ...................................................... 606/234
(58) Field of Search .............................. 606/234–236; 215/11.1, 11.5

(56) References Cited

U.S. PATENT DOCUMENTS

| | | | |
|---|---|---|---|
| 745,920 A | 1/1903 | Spencer | |
| 2,824,561 A | 2/1958 | Mueller | 128/252 |
| 2,889,829 A | 6/1959 | Tannenbaum et al. | 128/252 |
| 3,043,464 A | 7/1962 | Cerasari | 215/100 |
| 3,631,856 A | 1/1972 | Taylor | 128/208 |
| 4,192,307 A | 3/1980 | Baer | 128/252 |
| 4,726,376 A | 2/1988 | Dahan | 128/360 |
| 5,078,733 A | 1/1992 | Eveleigh et al. | 606/236 |
| 5,700,279 A | 12/1997 | Blando | 606/236 |
| 6,112,749 A | 9/2000 | Hall et al. | 128/898 |

FOREIGN PATENT DOCUMENTS

CH 679009 A5 12/1991

*Primary Examiner*—Kennedy Schaetzle
*Assistant Examiner*—Kristen Droesch
(74) *Attorney, Agent, or Firm*—Downs Rachlin Martin PLLC; Ratner & Prestia

(57) ABSTRACT

An osmophore-pacifier. The osmophore-pacifier contains an odorant. When the osmophore-pacifier is sucked by an infant, it releases an odor which stimulates sucking behavior in the infant. The osmophore-pacifier includes a nipple, a shield portion, a matrix containing the odorant, and an air channel for releasing the odor. The odorant may be replaced with a different type of odorant in order to determine which odor stimulates continued sucking of the osmophore-pacifier, to promote sucking behavior, and to calm or soothe an infant in a state of agitation or pain.

27 Claims, 6 Drawing Sheets

OSMOPHORE-PACIFIER

CROSS-REFERENCE TO RELATED APPLICATIONS

This application is a continuation of U.S. application Ser. No. 09/516,372, filed on Mar.1, 2000, now abandoned, and claims the benefit of priority of U.S. Provisional Application No. 60/122,333, filed on Mar. 2, 1999, the entire disclosure of which is incorporated by reference into this application.

FIELD OF THE INVENTION

The present invention is directed to infant pacifiers. More particularly, the present invention is directed to infant pacifiers which stimulate sucking behavior in infants.

BACKGROUND OF THE INVENTION

Many babies do not have fully developed or coordinated sucking and swallowing reflexes. Theses deficiencies may exist, for example, with tube-fed or premature babies. The use of conventional nipples and pacifiers is insufficient to stimulate sucking to improve these capacities. These deficiencies can prevent babies from obtaining the proper nourishment needed for healthy growth.

The promotion of non-nutritive sucking behavior in infants has been used as a remedy for the deficiencies. It is considered a valid therapeutic objective, because it accelerates recovery of feeding reflexes and promotes gastric motility. Past attempts to stimulate sucking have incorporated tactile stimuli, taste stimuli, flavored or scented pacifiers, or any combination of the three.

Nevertheless, taste stimuli have not proved to be therapeutically successful. In addition, certain pacifiers which provide some flavor or scent to the infant, but which are not dependent on the sucking activity of the infant, do not act as direct stimuli. Thus, there is a need to improve on conventionally used tactile stimuli and other flavors or scents presently used to encourage infant sucking.

SUMMARY OF THE INVENTION

To meet this and other needs, and in view of its purposes, the present invention provides a pacifier including a mechanism for generating an odor which stimulates sucking behavior. As an infant user sucks on the pacifier, the sucking causes an odor to be generated from the pacifier in a location proximate to the infant's nostrils. The odor is preferably a pleasant odor, which encourages the infant to continue sucking. The infant is operatively conditioned to suck on the pacifier so that it produces the odor, thus encouraging the infant's sucking and feeding reflexes.

In one embodiment of the present invention, the pacifier contains a nipple which, when sucked, causes the pacifier to release an odor which stimulates sucking behavior in, for example, an infant. The odor release may be prompted by a pressure differential in the pacifier, fluid flow or evaporation, any combination of those factors, or any other suitable mechanism which causes the odor to be released when the pacifier is sucked.

In a preferred embodiment of the present invention, the pacifier contains a housing, a shield, an odorant (i.e., odor source), air channels, and a nipple which, along with the housing, creates an airspace. When the nipple is sucked by an infant, the airspace is reduced which forces air across the odorant, thus picking up the scent. The odor proceeds through the air channels to outside of the shield where the scent is detected by the infant.

In another embodiment of the present invention, the pacifier is used in a method of diagnosing what odor or odors are pleasing. The pacifier can be used, according to this method, to stimulate feeding reflexes in infants by testing the pacifier using different odors and observing whether different odors act as sucking stimuli. In yet another embodiment of the present invention, the pacifier is used in a method of operant-conditioning an infant to stimulate feeding reflexes by providing the infant with the pacifier, such that sucking of the pacifier by the infant produces a pleasant odor for the infant, and allowing the infant to continue sucking. In a further embodiment of the present invention, the pacifier is used to calm or soothe an infant in a state of agitation or pain.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
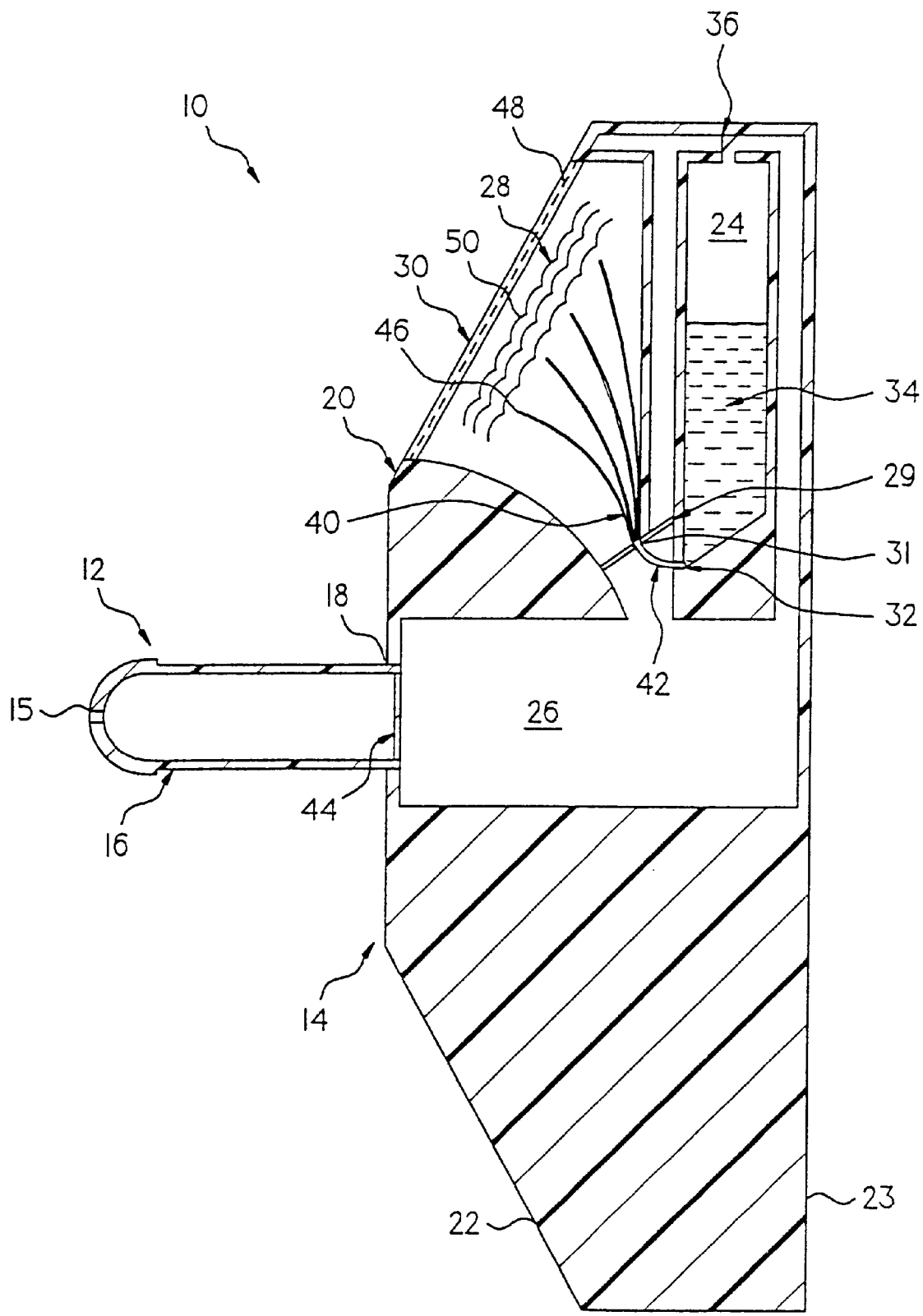
FIG. 1 if a cross-sectional view of a first embodiment of the pacifier of the present invention.

Certain terminology is used in the following description for convenience only and is not intended to limit the scope of the invention in any way. The words "right,""left,""lower," " and "upper" designate directions in the drawing s to which reference is made. The words "inwardly" and "outwardly" refer to directions towards and away from, respectively, the geometric center of the pacifier and designated parts of the pacifier in accordance with the present invention. The terminology includes the words noted above as well as derivatives of those words and words of similar import.

The pacifier of the present invention is intended to be used primarily in the treatment and prevention of feeding difficulty in infants. Use of the pacifier of the present invention is based on an operant-conditioning principle, i.e., using an odor as a reward for sucking behavior. This strategy is based on the premise that an olfactory cue can act as a positive reinforcer for sucking behavior because infants are known to be oriented to olfactory stimuli. The characteristics of neonatal olfaction that make it a good choice for promoting non-nutritive sucking include: (1) there is strong evidence that infants normally learn by using olfactory cues, and that certain olfactory sensations have intrinsic hedonic value for neonates; (2) olfactory stimuli are known to play an important role in organizing and orienting oral appetite behavior in infants; and (3) the potential for toxicity from repeated exposure to a purely olfactory stimulus is negligible.

Thus, the present invention is directed to a pacifier incorporating an olfactory stimulus (odor), optionally with a tactile stimulus (nipple), to encourage sucking behavior in infants. The two combined types of stimuli are more effective than conventionally used tactile stimuli alone. The olfactory stimulus is especially needed in those infants with a weak response to tactile stimuli. Further, the response of an infant to the olfactory stimulus may provide information on an infant's flavor preferences and an approximate restoration of odor experience to tube-fed infants may be beneficial beyond stimulating non-nutritive sucking behavior.

Figure 2:
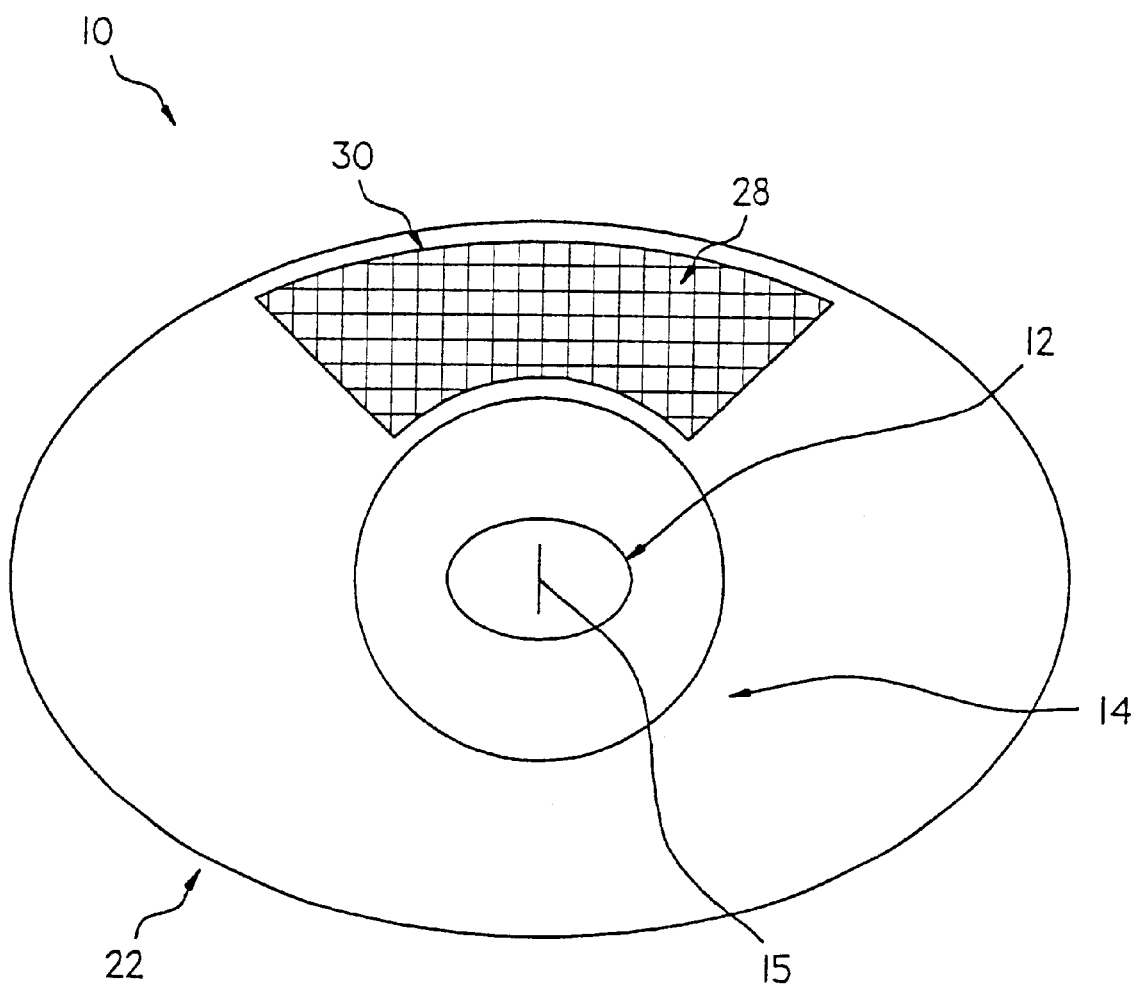
FIG. 2 is a front view of the first embodiment of the pacifier of the present invention.

Referring to the drawing, in which like numbers indicate like elements throughout, there is shown in FIGS. 1 and 2 an osmophore-pacifier 10 in accordance with the present invention. The osmophore-pacifier 10 includes a nipple 12 and a shield 14 generally similar in shape to that of a typical pacifier. The nipple 12 is hollow and includes an exterior wall 16 that is placed in the infant's mouth. The remainder of the osmophore-pacifier 10 is extra-oral. The shield 14 is attached to an outer perimeter 18 of an open end of the nipple 12 and is large enough to prevent the shield 14 from being inserted into the infant's mouth. The shield 14 has a superior edge 20 which, when the osmophore-pacifier 10 is properly inserted into the infant's mouth, is located between the infant's upper lip and nostrils.

A housing 22 is provided on the shield 14 distal from the nipple 12. The housing 22 and the shield 14 generally comprise a base 23. The housing 22 may be separate from the shield 14 or formed within the shield 14. The housing 22 encloses an odorant reservoir 24, a wick chamber 26, and an osmophore 28. Preferably, the housing 22 is made of plastic, but those skilled in the art will understand that other suitable materials can be used.

The outward appearance of the osmophore-pacifier 10 is not much different than that of a typical pacifier, with the exception that the extra-oral part of the osmophore-pacifier 1O is somewhat larger and deeper than the typical pacifier due to the odorant reservoir 24. An opening is located through the housing 22 proximate the superior edge 20 of the shield 14 so that, when the osmophore-pacifier 10 is in the infant's mouth, the opening is located proximate to the infant's nose. The opening may be covered by a removable grid 30 or partially covered by a removable panel to retain the osmophore 28 in the osmophore-pacifier 10.

Preferably, the reservoir 24 inside the housing 22 is funnel-shaped, tapering to a small aperture 32 which is located at the bottom of the reservoir 24 when the osmophore-pacifier 10 is in use, as shown in FIG. 1. An odorant solution 34 is contained within the reservoir 24. The shape of the reservoir 24 and the small size of the aperture 32 minimize the reservoir-draining effect of the hydrostatic pressure which is naturally exerted by the odorant solution 34 on the area of the aperture 32 compared to the effect of the surface tension of the odorant solution 34 at the aperture 32. This configuration tends to keep the odorant solution 34 within the reservoir 24. Preferably, the capacity of the reservoir 24 is less than three milliliters, although the capacity of the reservoir 24 can be equal to or greater than three milliliters. The reservoir 24 includes a vent 36 located on the housing 22 that vents the reservoir 24 to the surrounding atmosphere and prevents a negative pressure from being formed in the reservoir 24 as the odorant solution 34 is drawn out.

The aperture 32 fluidly connects the reservoir 24 to the wick chamber 26 within the housing 22. A wick 40 is located in the wick chamber 26, with a first wick end 42 extending toward the aperture 32. Preferably, the first wick end 42 is tubular so that capillary action draws the odorant solution 34 in the wick 40. Preferably, a second end 46 of the wick 40 opens into the osmophore 28. Preferably, the wick 40 is comprised of material, such as cellulose, silicone, or cogeners of those materials, that maximizes the diffusion or the odorant solution 34 through the wick 40 and along a concentration gradient through capillary action. Moreover, those skilled in the art will realize that other suitable materials can be used.

It is preferred that the wick chamber 26 is under 1.0 milliliter in capacity and is separated from the nipple 12 by an elastic diaphragm 44. The elastic diaphragm 44 and the nipple wall 16 form a chamber within the nipple 12. The nipple 12 may or may not have a through hole 15 which aids in displacing the diaphragm 44 toward the hole 15 as the infant sucks on the nipple 12.

The wick chamber 26 is separated from the osmophore 28 by a wick seal 29. The wick 40 extends through the wick seal 29 at a seal hole 31. The purpose of the wick seal 29 is to form a closed or at least substantially closed wick chamber 26 so that deflection of the diaphragm 44 toward the infant's mouth, when the infant sucks properly, creates a negative pressure within the wick chamber 26 and draws the odorant solution 34 out of the reservoir 24.

An "osmophore" is commonly defined as a surface from which a volatile compound evaporates and, for the purpose of this application, can include any mechanism for release of a scent or odor. To promote evaporation, an osmophore generally has a large evaporative surface area. The osmophore 28 of the osmophore-pacifier 10 preferably has surface structural characteristics modeled after the osmophore of an insect-pollinated flower, such as an orchid. The osmophore 28 lies on a superior surface 48 of the wick chamber 26 and is continuous with the superior edge 20 of the shield 14 so that a superior surface 50 of the osmophore 28 is in fluid communication with the atmosphere through the opening covered by grid 30 in the housing 22. The osmophore 28 is thus exposed to the air under the infant's nose at a fixed distance of preferably less than one centimeter from the infant's nostrils when the osmophore-pacifier 10 is in the infant's mouth. The osmophore 28 and the wick 40 are removable from the osmophore-pacifier 10 by first removing the grid 30 over the opening in the housing 22 and then removing the osmophore 28 and the wick 40.

Preferably, the odorant solution 34 which i s contained in the reservoir 24 is made up of an organic acid such as lactic, citric, or butyric acid or vanillan, lactones, or other simple organic compounds found in milk as the active ingredient , although tho se skilled in the art will understand that other active ingredients can be used as the odorant. Any active ingredient that is pleasing to infants such that it stimulates sucking behavior, can be used. The odorant solution 34 can be formed by dissolving organic compounds at fixed concentrations in a aqueous or oil-based solution.

To fill the reservoir 24, the odorant solution 34 is dropped directly onto the superior surface 50 of the osmophore 28 through the opening covered by the grid 30. Capillary action and the reservoir vent 36 allow the odorant solution 34 to flow in reverse from the osmophore 28, through the wick 40 and into the reservoir 24. The vent 36 also allows the reservoir 24 to empty during us e without creating a negative pressure in the reservoir 24.

In operation, the osmophore-pacifier 10 is inserted into the infant's mouth, with the opening covered by grid 30 on the housing 22 located so that the superior surface 50 of the osmophore 28 is exposed under the infant's nose. As the infant sucks, the elastic diaphragm 44 is drawn into the hollow of nipple 12, causing a suction within the housing 22 The suction partially saturates the wick 40 by overcoming the surface tension of the odorant solution 34 at the aperture 32, drawing the odorant solution 34 into the wick chamber 26 and onto the wick 40. Passive diffusion of the odorant solution 34 through the wick 40 distributes the odorant solution 34 to the osmophore 28.

The amount of odorant solution 34 delivered to the wick 40 reflects the combined forces of the infant's suck; the surface tension of the odorant solution 34; hydrostatic and electrostatic forces between the wick 40, the odorant solution 34, and the housing 22; and the distance between the aperture 32 and the wick 40. This distance can be adjusted according to the power of the infant's suck. To decrease the amount of odorant solution 34 delivered, the wick 40 can be pulled away from the aperture 32. In addition, to increase the amount of odorant solution 34 delivered, the wick 40 can be inserted closer to the aperture 32.

The nipple 12 and the diaphragm 44 work together as a pump which is activated by the infant's suck (not shown) to draw the odorant solution 34 from the reservoir 24 to the wick 40 where it passes through the wick 40 to the superior surface 50 of the osmophore 28. Evaporation of the odorant solution 34 at the superior surface 50 of the osmophore 28 sets up a chemical concentration gradient which exists until the wick 40 is desaturated with the odorant solution 34. Once the infant's suck initiates the flow of odorant solution 34 along the wick 40, diffusion of the odorant solution 34 through the wick 40 draws the odorant solution 34 toward the superior surface 50 of the osmophore 28 where it evaporates and is inhaled by the infant.

Preferably, the kinetic properties of the wick 40, the osmophore 28, the odorant solution 34, and the reservoir 24 are such that the smell of the odorant solution 34 can be detected within one second of the suck. Preferably, the molecular weight of odorants in solution 34 is less than 800 Daltons, although the molecular weight of the odorants 34 can equal or exceed 800 Daltons. Preferably, the smell intensity attenuates to neutral less than three seconds after a single suck.

It may be desirable to use an alternate odorant solution if the infant does not respond to the original odorant solution 34 in the osmophore-pacifier 10. The original odorant solution 34 can be removed from the osmophore-pacifier 10 and replaced by the alternate odorant solution. The original wick 40 and osmophore 28 will be saturated with the original odorants solution 34 and it will be desirable to replace the wick 40 and the osmophore 28 as well. Preferably, the wick 40 and the osmophore 28 can be replaced by removing the grid 30 from the opening in the housing 22, removing the osmophore 28 and the wick 40 from the wick chamber 26, inserting a new wick 40 and a new osmophore 28, and replacing the grid 30 in the opening in the housing 22. The odorant solution 34 can be emptied from the reservoir 24 by allowing the odorant solution 34 to drain out from the vent 36.

It is preferred that the elastic diaphragm 44 be used to pump the odorant solution 34 from the reservoir 24 to the osmophore 28. Other mechanisms can be used, however, to perform that function. For example, a pump can expel the odorant solution 34 from the osmophore-pacifier 10. These mechanisms are powered by deformation of the nipple 12 due to sucking.

In addition, although evaporation of a liquid odorant solution is presently preferred, it would be appreciated that an odorant might be provided in solid form and released directly by sublimation to a vapor at ambient or body temperature or as solid particles of a very fine powder and carried away in an air stream generated by sucking the nipple.

Figure 3:
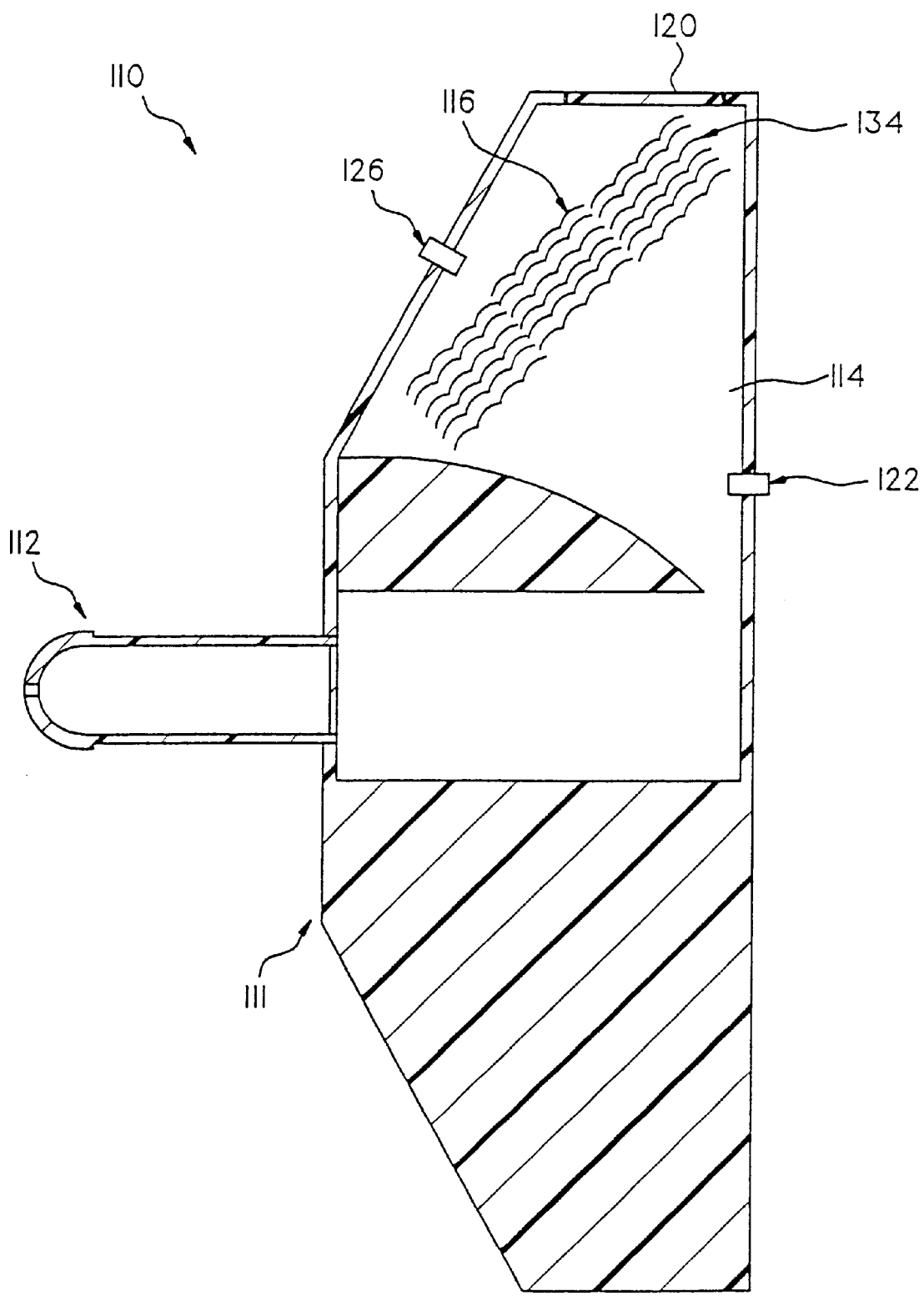
FIG. 3 is a cross-sectional view of a second embodiment of the pacifier of the present invention.

A second embodiment, which produces an odor without the need for a liquid solution, is shown in FIG. 3. An osmophore-pacifier 110 comprises a housing 111, a nipple 112, a scent chamber 114, and an osmophore 116. The scent chamber 114 is accessed by a sealable hatch 120 which is located adjacent to the osmophore 116. The hatch 120 permits a scent-bearing fibrous material 134 to be inserted into the scent chamber 114. A one-way valve 122 (e.g., a duck-bill valve) located on the osmophore-pacifier 110 between the scent chamber 114 and the atmosphere allows air to be drawn into the scent chamber 114 upon sucking on the nipple 112. The one-way valve 122 can be made from material such as pliant silicone, although those skilled in the art will understand that other types of one-way valves and materials can be used.

Release of suction (not shown) causes an over-pressure within the scent chamber 114. The over-pressure is relieved by air escaping from a second one-way valve 126 located adjacent to the osmophore 116. The air travels through the osmophore 116, and out of the osmophore-pacifier 110, where it is inhaled by the infant. As the air travels through the osmophore 116, the air picks up the odor from the scent-bearing fibrous material 134.

Figure 4:
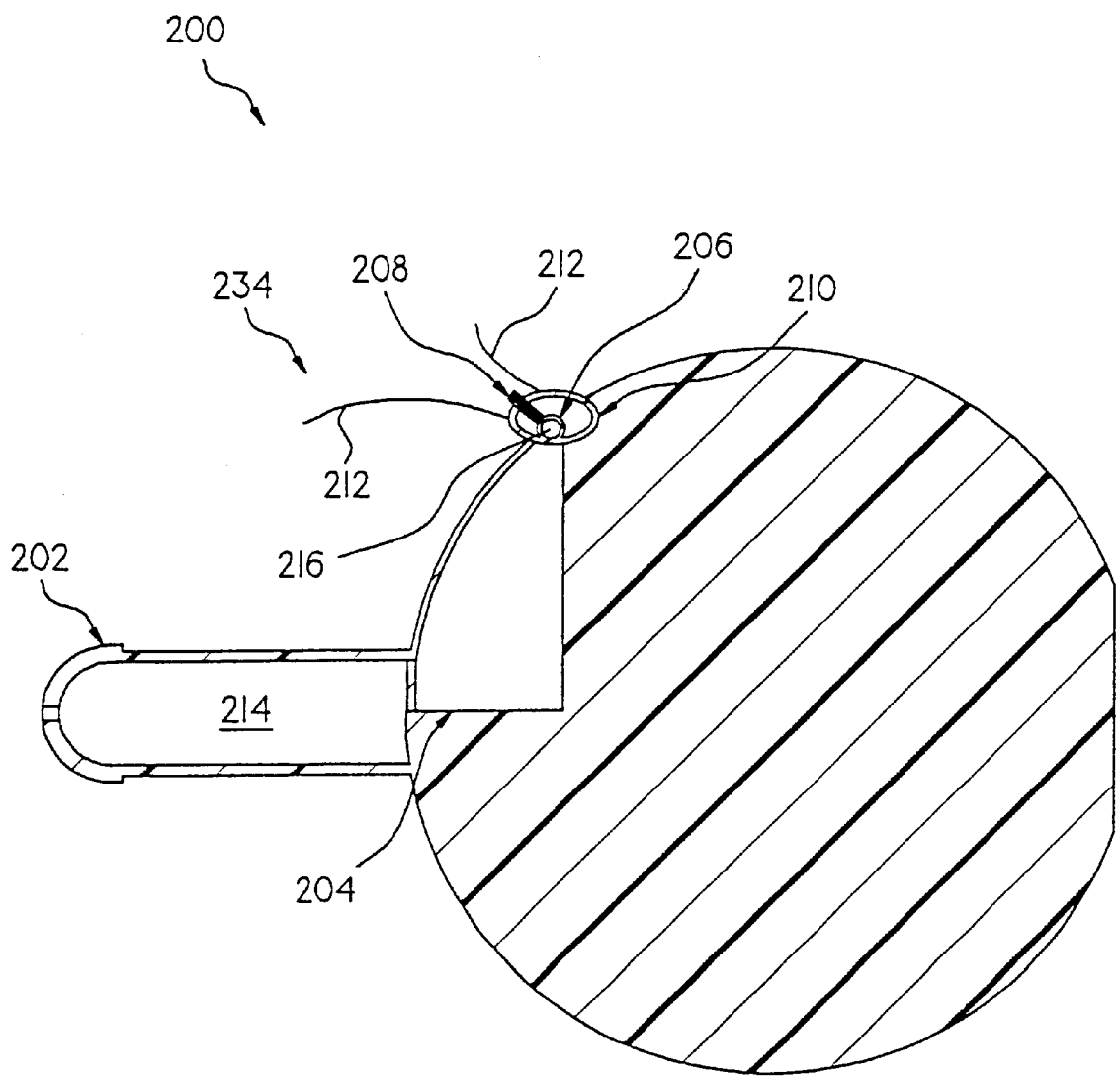
FIG. 4 is a cross-sectional view of a third embodiment of the pacifier of the present invention.

In the third embodiment, shown in FIG. 4, an osmophore-pacifier 200 includes a distensible nipple 202, a siphon 204, and osmophore pump 206, a jet 208, a sealed pump chamber 210, and osmophore petals 212. Preferably, the osmophore 200 is made of all-silicone construction and includes a detachable, porous, sponge-like silicone matrix onto which the odorant is placed (as indicated by arrow 234). The petals 212 may be cobbled to increase their surface areas, and are treated intermittently with a volatile liquid odorant, such as a weak mixture of lactate and butyric acids.

Sucking by the infant (not shown) on the distensible nipple 202 creates a negative pressure within the lumen 214 of the nipple 202, which is transmitted by the siphon 204 to the sealed pump chamber 210. The negative pressure expands the osmophore pump 206 as air flows into its lumen 216 via the jet 208. Preferably, the osmophore pump 206 is made from thin-walled, balloon-like silicone and the jet 208 is made of rigid, thick-walled silicone. With the release of the infant's suck, the osmophore pump 206 collapses, expressing air through the jet 208 and obliquely along the osmophore petals 212. The flume of air expressed from the jet 208 picks up the volatile scent from the osmophore petals 212 and carries the scent toward the infant's nostrils. It will be appreciated that the lumen 214 and the jet 208 can be coupled through an elastic diaphragm or similar pump elements in other suitable ways known to those skilled in the art.

Figure 5:
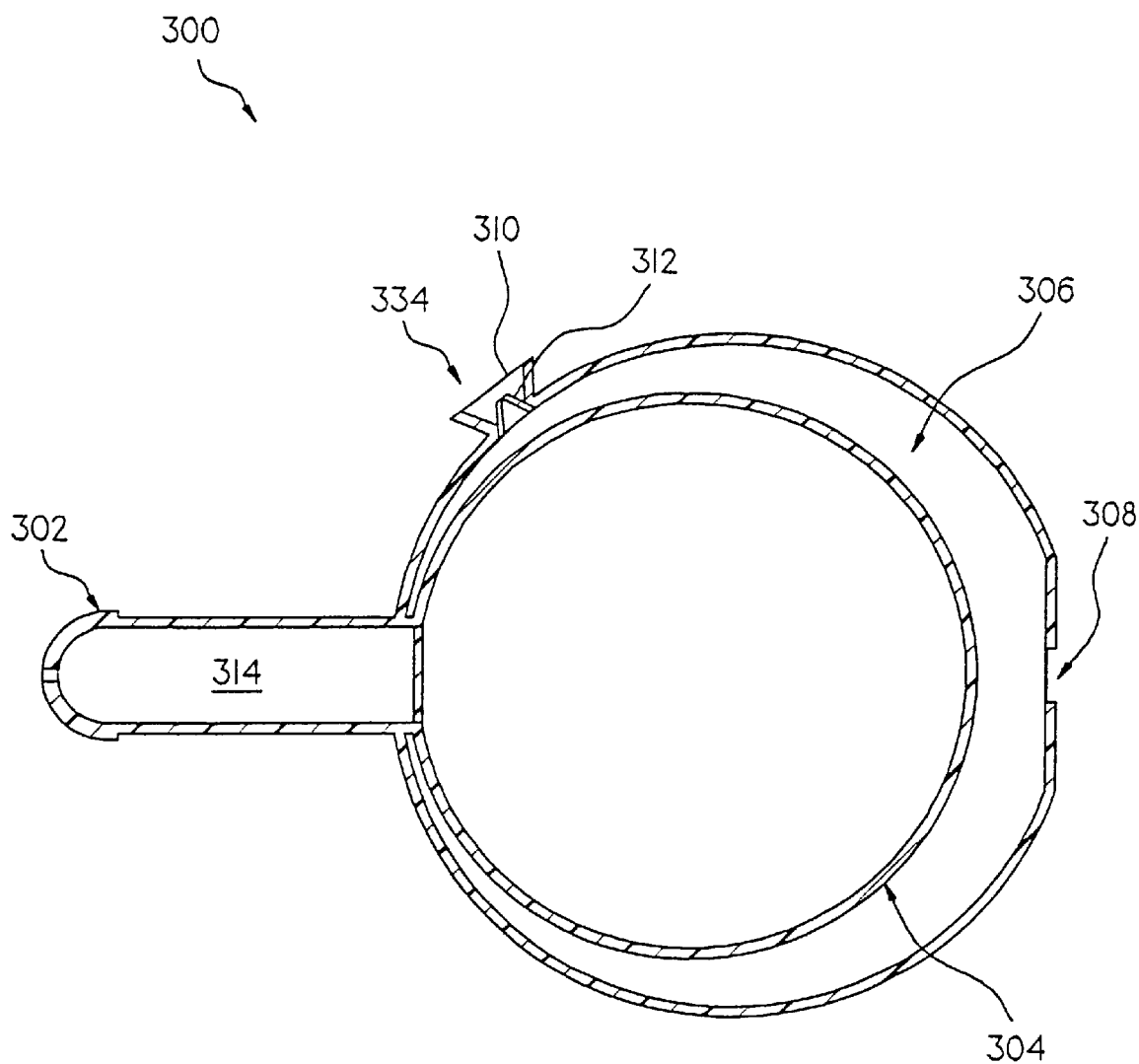
FIG. 5 is a cross-sectional view of a fourth embodiment of the pacifier of the present invention.

In a fourth embodiment, shown in FIG. 5, the osmophore pacifier 300 includes a distensible nipple 302, an osmophore bellows 304, a vapor chamber 306, a one-way intake valve 308, and an osmophore 310. A one-way (e.g., duck-bill) valve 312 lies at the base of the osmophore 310, which consists of a detachable, porous, sponge-like matrix of silicone or similar material onto which the odorant (indicated by arrow 334) is placed.

Sucking by the infant (not shown) on the distensible nipple 302 creates a negative pressure in the lumen 314 of the nipple 302, which is transmitted via contraction of the osmophore bellows 304 to the vapor chamber 306. Outside air is thereby drawn in to the vapor chamber 306 via the one-way air intake valve 308. With the release of the infant's suck, the bellows 304 re-expands, expressing air through the duckbill valve 312 at the base of the osmophore 310, and creating a current through the osmophore 310. This current of air becomes scented, and the scent is carried towards the infant's nose by convection and from the expansion of the bellows 304.

Figure 6A:
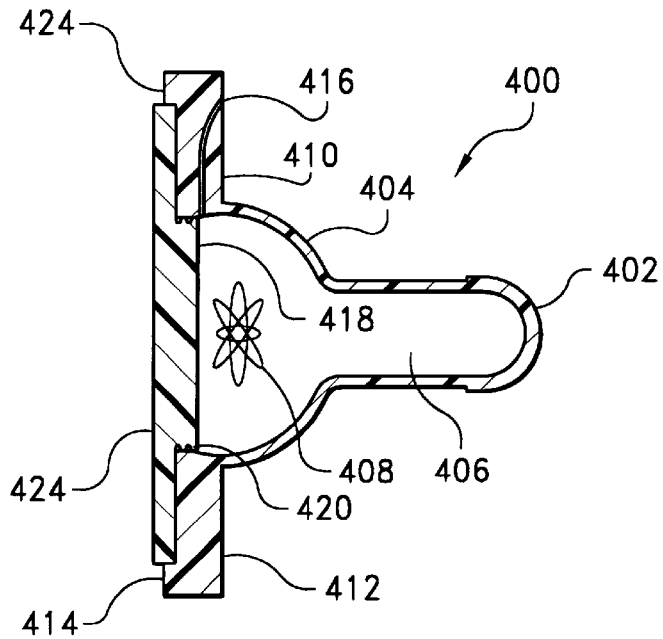
FIG. 6A is a cross-sectional view of a preferred embodiment of the pacifier of the present invention.
Figure 6B:
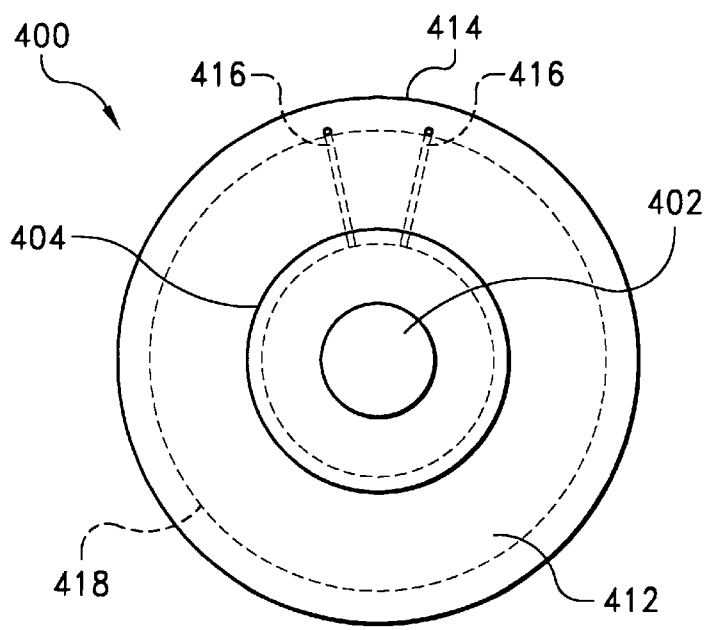
FIG. 6B is a frontal elevational view of the pacifier shown in FIG. 6A.

In a preferred embodiment of the present invention, as shown in FIGS. 6A and 6B, the osmophore-pacifier 400 includes a nipple 402 and a hilt 404, which together generally enclose a lumen (airspace) 406. The housing 414 of the osmophore-pacifier 400 contains a shield 412 and an opening in which the rear shield 424 is removably secured by a form fit. The ribs 420 of the plug 418 of the rear shield 424 contact the outside of the opening in the housing 414 to form an airtight seal 422. The rear shield 424 may be attached to the housing 414 by a mechanism other than the plug 418 and pivoted by a hinge or other suitable device to maintain access to the lumen 406. Alternatively, the rear shield 424 may be a separate part from the housing 414. In any case, the rear shield 424 may be attached to the opening in the housing 414 at an angle, such as a 45° angle, to further ensure the airtight seal 422.

Inside the lumen 406 and held in the hilt 404, a sponge or matrix 408, constructed of cotton, polyethylene, or any other suitable porous material containing an odorant is inserted by removing or pivoting the plug 418 of the rear shield 424 from the housing 414, placing the matrix 408 in the hilt 404, and replacing the rear shield 424 to form the airtight seal 422.

When the nipple 402 is placed in an infant's mouth and the infant (not shown) sucks on the nipple 402, the lumen 406 is compressed and air is forced across the matrix 408, picking up the scent, into one or more air channels 410 starting in the hilt 404 and running through the shield 412 and out of the shield 412 through openings 416 in the shield 412. When the osmophore-pacifier 400 is properly inserted into the infant's mouth, the openings 416 are located between the infant's upper lip and nostrils. The scent will further stimulate sucking by the infant and further compression of the air space in the lumen 406, thus expelling more odor into the nasal area of the infant to continue stimulation. The amount and type of odorant can be adjusted to account for the force which an infant sucks the pacifier, the scents which stimulate an infant, or both.

The osmophore-pacifier 10, 110, 200, 300, 400 is used in operant-conditioning of an infant to stimulate feeding reflexes. The infant is provided with the osmophore-pacifier 10, 110, 200, 300, 400 so that sucking of the osmophore-pacifier 10, 110, 200, 300, 400 by the infant produces a pleasant odor for the infant. The sucking on the osmophore-pacifier 10, 110, 200, 300, 400 stimulates and promotes maturation of feeding reflexes. The odor rapidly dissipates, so that, in order to reproduce the odor, the infant must continue sucking on the osmophore-pacifier 10, 110, 200, 300, 400. By repeatedly sucking on the osmophore-pacifier 10, 110, 200, 300, 400 and producing a pleasant odor, the infant is operantly conditioned to associate the pleasant odor with sucking. This increase in non-nutritive sucking behavior is expected to promote healthy feeding reflexes.

Initially, it is not known what particular odor or odors may be pleasant to an individual infant. The osmophore-pacifier 10, 110, 200, 300, 400 can be used to diagnose what odor or odors are pleasing or more pleasing to the infant in order to determine which odor or odors can be used to stimulate feeding reflexes. The infant is provided with the osmophore-pacifier 10, 110, 200, 300, 400 which contains a particular odorant so that sucking of the osmophore-pacifier 10, 110, 200, 300, 400 by the infant produces an odor. If the odor which is produced is pleasing to the infant, the infant will continue to such on the osmophore-pacifier 10, 110, 200, 300, 400 to continue producing the odor. If it is determined that the odor produced is pleasing to the infant, the diagnosis determination can be terminated. If the odor which is produced is not pleasing to the infant, the infant will cease sucking on the osmophore-pacifier 10, 110, 200, 300, 400. The odorant in the osmophore-pacifier 10, 110, 200, 300, 400 is then replaced with a new, different odorant, and the process of diagnosing whether the new odor is pleasing to the infant, or whether yet a different odor must be used, is repeated until it is determined which odor promotes sucking of the osmophore-pacifier 10, 110, 200, 300, 400 to continue production of that odor.

The osmophore-pacifier 10, 110, 200, 300, 400 can be used to treat an infant in a state of agitation or pain. The infant is provided with the osmophore-pacifier 10, 110, 200, 300, 400 which contains a particular odorant so that sucking of the osmophore-pacifier 10, 110, 200, 300, 400 by the infant produces an odor pleasing to the infant. The infant can then be allowed to continue sucking of the pacifier until the infant is calmed or soothed.

The pacifier 10, 110, 200, 300, 400 of the resent invention can be further adapted incorporating any suitable individual mechanism used in any embodiment of the present invention. The features of the pacifier 10, 110, 200, 300, 400 may be further adjusted to account for behavior of the individual infants.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An osmophore-pacifier for stimulating sucking behavior in an infant having a nose comprising: a nipple, a non-medicinal odorant, and a non-electrically powered means for releasing said non-medicinal odorant, wherein said non-electrically-powered means releases said non-medicinal odorant in response to the sucking behavior.

2. An osmophore-pacifier according to claim 1, wherein said odorant has the odor of food.

3. An osmophore-pacifier according to claim 1, wherein said non-electrically powered means comprises a pump.

4. An osmophore-pacifier according to claim 1, wherein said pump is a diaphragm pump.

5. An osmophore-pacifier according to claim 1, further comprising a matrix, a lumen and a hilt attached to said nipple and defining at least a portion of said lumen, at least a portion of said matrix being located in said portion of said lumen defined by said hilt.

6. An osmophore-pacifier according to claim 5, further comprising a shield attached to said hilt opposite said nipple, said shield having an outer region located proximate the nose of the infant when the infant is using the osmophore-pacifier, said shield containing at least one air channel forming an elongate passageway extending between said lumen and said outer region.

7. An osmophore-pacifier for utilizing an odorant to stimulate sucking behavior in an infant having a nose and capable of performing a sucking motion, comprising:
- a nipple;
- an osmophore for providing the odorant extra-orally adjacent the nose of the infant; and
- means for releasing the odorant non-electrically via said osmophore when the pacifier is sucked by the infant, wherein said means is separate from said nipple and the sucking motion of the infant causes the release of the odorant.

8. An osmophore-pacifier according to claim 1, wherein said means for releasing the odorant comprises a pump mechanism.

9. An osmophore-pacifier according to claim 8, wherein said pump mechanism comprises a siphon.

10. An osmophore-pacifier according to claim 8, wherein said pump mechanism comprises a jet.

11. An osmophore-pacifier according to claim 8, further comprising a hilt attached to said nipple, wherein said pump mechanism includes said hilt.

12. An osmophore-pacifier according to claim 11, wherein said hilt defines a lumen and said osmophore comprises a matrix contained at least partially within said lumen.

13. An osmophore-pacifier according to claim 12, further comprising:
- a housing attached to said hilt generally opposite said nipple, said housing having an outer region located adjacent the nose of the infant when the infant is sucking on said nipple; an d
- at least one air channel located within said housing and forming an elongate passageway extending between said lumen and said outer region.

14. An osmophore-pacifier according to claim 8, wherein said nipple defines an airspace and the osmophore-pacifier further comprises a chamber and a diaphragm located between said airspace and said chamber, said pump mechanism comprising said diaphragm.

15. An osmophore-pacifier according to claim 7, further comprising a reservoir for storing the odorant, said reservoir being spaced from said osmophore.

16. An osmophore-pacifier according to claim 15, wherein said means for releasing the odorant comprises a wick extending between said reservoir and said osmophore.

17. An osmophore-pacifier according to claim 16, wherein said wick comprises at least one capillary tube.

18. An osmophore-pacifier according to claim 7, further comprising a housing defining a chamber containing said osmophore and at least one one-way valve located between said chamber and the environment surrounding the osmophore-pacifier.

19. An osmophore-pacifier according to claim 18, comprising two one-way valves, each located between said chamber and the environment surrounding the osmophore-pacifier.

20. An osmophore-pacifier according to claim 7, wherein said nipple defines a lumen and contains an opening extending between said lumen and the environment surrounding said nipple.

21. An osmophore-pacifier according to claim 7, wherein said means for releasing the odorant comprises osmophore petals.

22. An osmophore-pacifier for stimulating the sucking behavior of an infant having a nose using an odorant, comprising:
- a lumen;
- a hilt defining at least a portion of said lumen;
- a matrix at least partially contained in said at least a portion of said lumen defined by said hilt, said matrix for holding the odorant; and
- a shield attached to said hilt, said shield having an outer region located adjacent the nose of the infant when the infant is using the osmophore pacifier and including at least one air channel forming an elongate passageway extending between said lumen and said outer region.

23. An osmophore-pacifier according to claim 22, wherein said shield includes an opening extending between said lumen and an environment surrounding the osmophore-pacifier, the osmophore pacifier further including a removable plug for alternatingly sealing said opening and allowing access to said lumen.

24. An osmophore-pacifier for stimulating the sucking behavior of an infant having a nose and lips using an odorant comprising:
- a lumen;
- a hilt defining at least a portion of said lumen;
- a matrix contained at least partially within said at least a portion of said lumen defined by said hilt; and
- a means for preventing the infant from ingesting the osmophore-pacifier, said means including a first outer region confronting the lips of the infant and a second outer region located adjacent the nose of the infant when the infant is using the osmophore-pacifier, the means further including a passageway extending between said lumen and said second outer surface for delivering the odorant adjacent the nose of the infant.

25. A method of operant-conditioning an infant to stimulate feeding reflexes comprising the steps of:
  (a) providing the infant with the osmophore-pacifier of claim 1 such that sucking of the pacifier by the infant produces a pleasant odor for the infant;
  (b) allowing the infant to continue sucking of the pacifier to produce the pleasant odor; and
  (c) repeating steps (a) and (b) to promote development of feeding reflexes using the odor as a reward.

26. A method of diagnosing an odor as a positive stimulus for altering the behavior patterns of an infant comprising the steps of:
  (a) providing the infant with the osmophore-pacifier of claim 1 so that sucking of the pacifier by the infant produces an odor;
  (b) diagnosing whether the presence of the odor promotes continued sucking of the osmophore-pacifier by the infant to continue production of the odor;
  (c) replacing the odorant solution in the osmophore-pacifier with a different odorant solution; and
  (d) repeating steps (a) through (c) until it is diagnosed what odor promotes sucking of the osmophore-pacifier by the infant to continue production of the odor.

27. A method of treating an infant in a state of agitation or pain comprising the steps of:
  (a) providing the infant with the osmophore-pacifier of claim 1 such that sucking of the pacifier by the infant produces a pleasant odor for the infant; and
  (b) allowing the infant to continue sucking of the pacifier to calm or soothe the infant.

* * * * *